United States Patent
Theofilos et al.

(10) Patent No.: US 9,498,350 B2
(45) Date of Patent: Nov. 22, 2016

(54) INSERTION DEVICE FOR USE WITH AN EXPANDABLE CAGE

(71) Applicant: K2M, Inc., Leesburg, VA (US)

(72) Inventors: Charles Theofilos, Palm Beach Gardens, FL (US); Adam Wassinger, Reston, VA (US); Todd Wallenstein, Ashburn, VA (US); John Donohoe, Sterling, VA (US)

(73) Assignee: K2M, Inc., Leesburg, VA (US)

( * ) Notice: Subject to any disclaimer, the term of this patent is extended or adjusted under 35 U.S.C. 154(b) by 324 days.

(21) Appl. No.: 14/060,060

(22) Filed: Oct. 22, 2013

(65) Prior Publication Data

US 2014/0114417 A1    Apr. 24, 2014

Related U.S. Application Data

(60) Provisional application No. 61/716,728, filed on Oct. 22, 2012.

(51) Int. Cl.
*A61B 17/58* (2006.01)
*A61F 2/46* (2006.01)
(Continued)

(52) U.S. Cl.
CPC .............. *A61F 2/4611* (2013.01); *A61F 2/447* (2013.01); *A61F 2/4455* (2013.01); *A61F 2002/30481* (2013.01); *A61F 2002/30556* (2013.01); *A61F 2002/30579* (2013.01); *A61F 2002/30774* (2013.01); *A61F 2002/30827* (2013.01); *A61F 2002/30836* (2013.01);
(Continued)

(58) Field of Classification Search
CPC .............. A61F 2/4603; A61F 2/4611; A61F 17/8841; A61F 2017/0046; A61F 2002/4624; A61F 17/7074; A61F 17/66; A61F 17/663; A61F 17/666; A61F 2017/681
See application file for complete search history.

(56) References Cited

U.S. PATENT DOCUMENTS

| 2005/0059976 | A1 | 3/2005 | Bryan et al. |
| 2005/0113842 | A1 | 5/2005 | Bertagnoli et al. |

(Continued)

FOREIGN PATENT DOCUMENTS

| WO | 2004/032807 A2 | 4/2004 |
| WO | 2008/065450 A1 | 6/2008 |
| WO | 2009/120618 A2 | 10/2009 |

OTHER PUBLICATIONS

European Search Report from corresponding EP 13189692 application dated Feb. 19, 2014.

*Primary Examiner* — Anu Ramana
(74) *Attorney, Agent, or Firm* — Carter, DeLuca, Farrell & Schmidt, LLP

(57) ABSTRACT

An insertion device includes a first engagement arm having a first body portion and a first proximal extension, a second engagement arm including a second body portion and a second proximal extension, and an adjustment mechanism. The second proximal extension is disposed about the first proximal extension and is slidable therealong to vary a spacing between the first and second engagement arms. The adjustment mechanism includes an adjustment screw rotatably coupled to the first proximal extension and an adjustment cylinder coupled to the second proximal extension. The adjustment cylinder is configured to receive the adjustment screw in threaded engagement therewith such that rotation of the adjustment screw relative to the adjustment cylinder urges the second proximal extension to translate along the first proximal extension to vary the spacing between the first and second engagement arms.

14 Claims, 15 Drawing Sheets

(51) Int. Cl.
*A61F 2/44* (2006.01)
*A61F 2/30* (2006.01)

(52) U.S. Cl.
CPC ............... *A61F 2002/30841* (2013.01); *A61F 2002/4475* (2013.01); *A61F 2002/4622* (2013.01); *A61F 2002/4623* (2013.01); *A61F 2002/4627* (2013.01); *A61F 2002/4628* (2013.01)

(56) References Cited

U.S. PATENT DOCUMENTS

2006/0167461 A1    7/2006   Hawkins et al.
2012/0130387 A1    5/2012   Simpson et al.

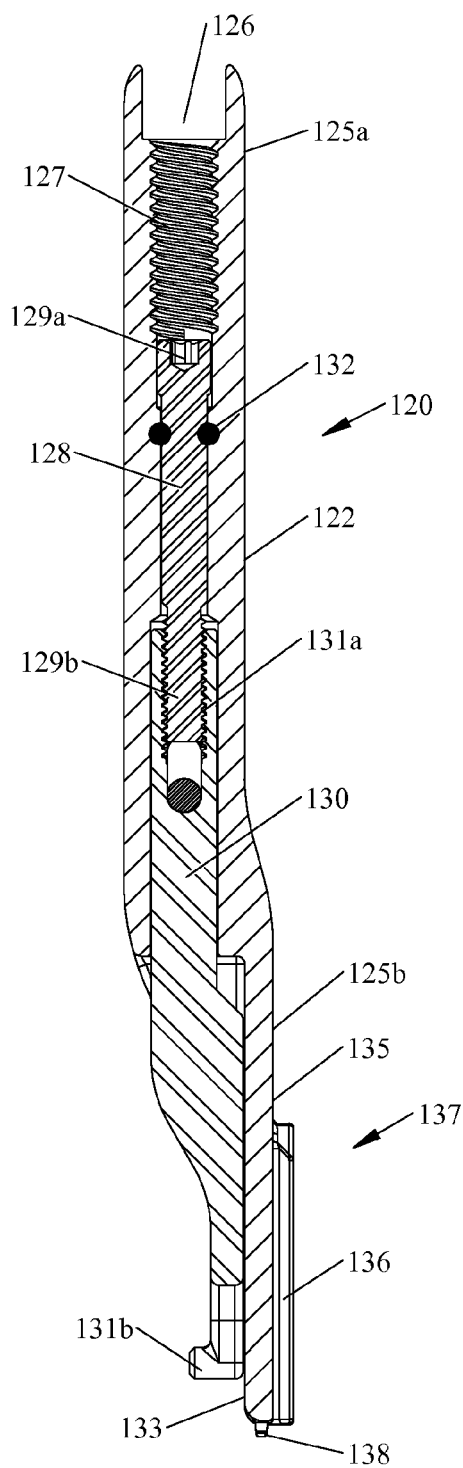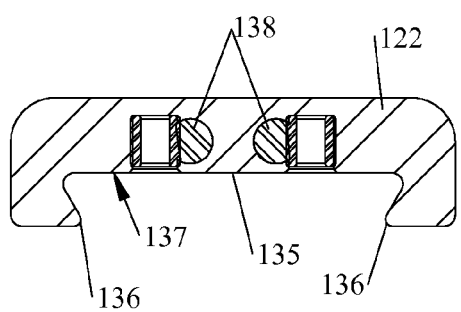
Fig. 8
Fig. 9

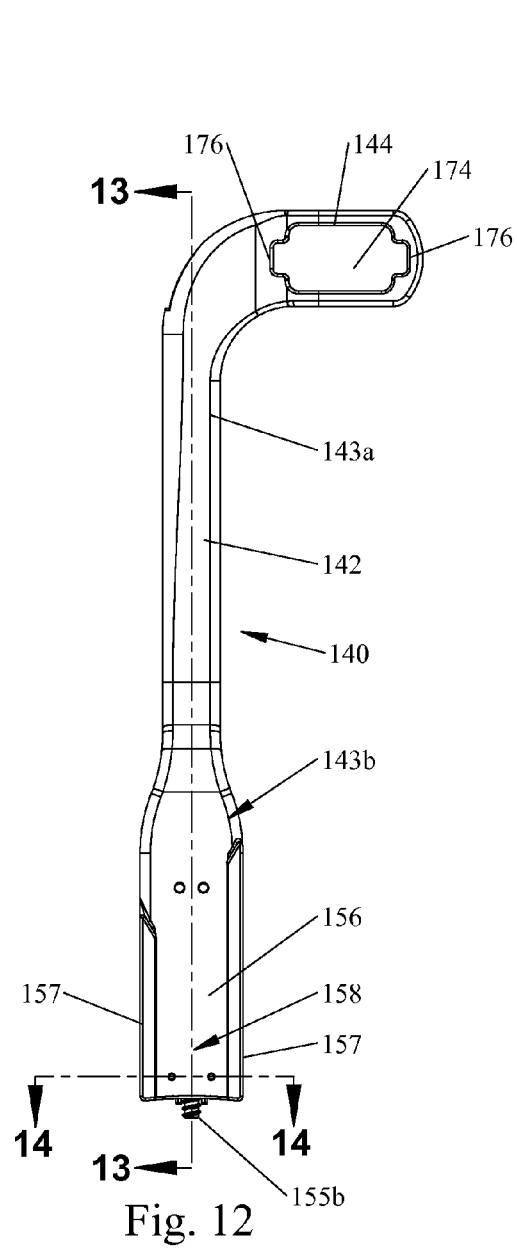
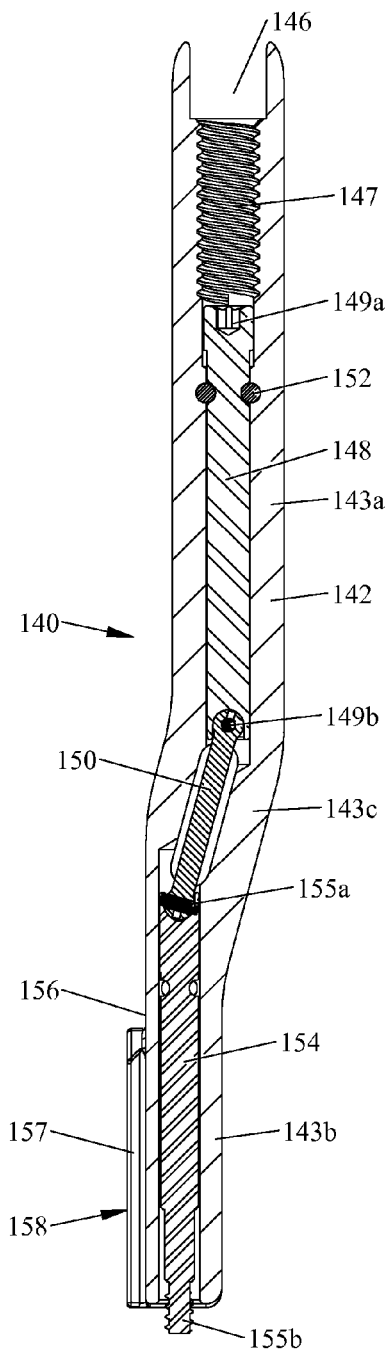
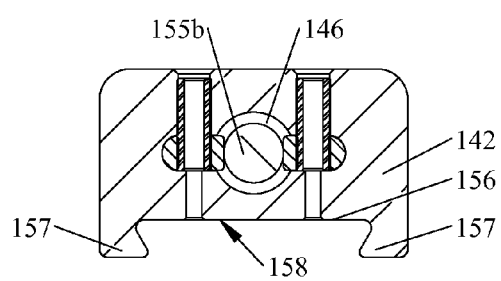
Fig. 12
Fig. 13
Fig. 14

US 9,498,350 B2

INSERTION DEVICE FOR USE WITH AN EXPANDABLE CAGE

CROSS-REFERENCE TO RELATED APPLICATIONS

This application claims the benefit of, and priority to, U.S. Provisional Patent Application No. 61/716,728, filed on Oct. 22, 2012, the contents of which are hereby incorporated herein by reference.

BACKGROUND

Technical Field

The present disclosure relates to devices and methods for treating spinal conditions and, more particularly, to an insertion device configured to facilitate insertion of an expandable cage into and positioning of the expandable cage within the intervertebral space to support adjacent vertebrae.

Background of Related Art

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves removal of the inter-vertebral discs. Corpectomy involves removal of the vertebral body as well as the adjacent inter-vertebral discs.

A number of spinal surgical devices may be used to promote bony fusion after decompressing the spinal nerves. For instance, surgeons often replace diseased vertebral tissue with one or more spinal cages and bone support matrix. Spinal cages support adjacent vertebral segments, while furthering spinal fusion of the adjacent vertebral bodies. As can be appreciated, insertion devices facilitate the insertion of such spinal cages into and positioning of such spinal cages within the intervertebral space to support the adjacent vertebral bodies.

SUMMARY

The present disclosure relates to an insertion device configured for use with an expandable cage. In embodiments, the insertion device includes a first engagement arm, a second engagement arm, and an adjustment mechanism. The first engagement arm includes a first body portion and a first proximal extension. The first body portion is configured to engage a first support member of an expandable cage. The second engagement arm includes a second body portion and a second proximal extension. The second body portion is configured to engage a second support member of the expandable cage. The second proximal extension is disposed about the first proximal extension and is slidable therealong from a free end of the first proximal extension to a fixed end of the first proximal extension to vary a spacing between the first and second engagement arms. The adjustment mechanism operably couples the first and second proximal extensions of the respective first and second engagement arms to one another and includes an adjustment screw and an adjustment cylinder. The adjustment screw is rotatably coupled to the first proximal extension and includes a shank defining threading. The adjustment cylinder is coupled to the second proximal extension and defines a threaded passageway configured to receive the shank of the adjustment screw in threaded engagement therewith. As such, rotation of the adjustment screw relative to the adjustment cylinder urges the second proximal extension to translate along the first proximal extension to vary the spacing between the first and second engagement arms.

In embodiments, the adjustment screw further includes a head configured to facilitate rotation of the adjustment screw relative to the adjustment cylinder.

In embodiments, the first engagement arm includes one or more protrusions configured for engagement within one or more corresponding apertures defined within the first support member of the expandable cage to engage the first support member at a distal end of the first engagement arm.

In embodiments, the second engagement arm includes a distal shaft extending distally from the second engagement arm. The distal shaft includes a threaded distal end configured for engagement within a threaded aperture defined within the second support member of the expandable cage to engage the second support member at a distal end of the second engagement arm.

In embodiments, the second engagement arm defines a longitudinal bore extending therethrough. In such embodiments, the distal shaft is disposed partially within and extends distally from the longitudinal bore. The longitudinal bore further includes a proximal shaft disposed therein and a linkage member disposed therein. The linkage member interconnects the proximal and distal shafts.

In embodiments, the proximal and distal shafts are laterally offset relative to one another. The linkage member, which interconnects the proximal and distal shafts, transfers rotational motion of the proximal shaft to rotational motion of the distal shaft.

In embodiments, the longitudinal bore of the second engagement arm is configured to receive an engagement tool configured to rotate the proximal shaft, thereby rotating the linkage member and the distal shaft for threadingly engaging the threaded distal end of the distal shaft within the threaded aperture of the second support member of the expandable cage.

In embodiments, the first engagement arm defines a longitudinal bore extending therethrough. In such embodiments, the longitudinal bore includes a screw member disposed therein and an indicator stop member partially disposed therein and extending distally therefrom. The screw member and the indicator stop member are coupled to one another such that rotation of the screw member effects translation of the indicator stop member relative to the first engagement arm to set an insertion depth limit.

In embodiments, the longitudinal bore of the first engagement arm is configured to receive a driver configured to rotate the screw member, thereby translating the indicator stop member relative to the first engagement arm.

In embodiments, the indicator stop member visually indicates the insertion depth limit.

In embodiments, an engagement tool is provided including a clip member engagement portion configured to couple to a clip member of the expandable cage at a distal end of the clip member engagement portion.

In embodiments, the first and/or second engagement arms define a track configured to guide insertion of the engagement tool to guide the clip member between the first and second support members of the expandable cage.

In embodiments, a handle portion is provided. In such embodiments, the handle portion extends from one of the first and second engagement arms and is configured to facilitate manipulation of the insertion device.

Methods of spinal surgery are also provided in accordance with the present disclosure. Initially, an intervertebral space is prepared. First and second engagement arms of an insertion device, e.g., such as the insertion device detailed herein, are engaged to first and second support members, respectively, of an expandable cage, e.g., such as the expandable cage detailed herein. The expandable cage is advanced, under control of the insertion device, into the intervertebral space. Next, the relative spacing between the first and second engagement arms is adjusted to adjust a height of the expandable cage within the intervertebral space. A clip member is coupled to a clip member insertion tool, e.g., such as the insertion tool detailed herein. The clip member insertion tool is moved relative to the insertion device such that at least a portion of the clip member insertion tool is guided by the insertion device to guide the clip member into engagement between the first and second support members of the expandable cage. Once this has been achieved, the clip member insertion tool is disengaged from the clip member and withdrawn from the surgical site and the insertion device is disengaged from the expandable cage and withdrawn from the surgical site.

BRIEF DESCRIPTION OF THE DRAWINGS

Various aspects and features of the present disclosure are described with reference to the accompanying drawing figures, wherein:

FIG. 8 is a cross-sectional view taken along section line 8-8 of FIG. 7;

FIG. 9 is a cross-sectional view taken along section line 9-9 of FIG. 7;

FIG. 12 is an outwardly-directed, side view of the insertion device of FIG. 1 showing the second engagement arm of the insertion device;

FIG. 13 is a cross-sectional view taken along section line 13-13 of FIG. 12;

FIG. 14 is a cross-sectional view taken along section line 14-14 of FIG. 12;

DETAILED DESCRIPTION OF THE EMBODIMENTS

Figure 1:
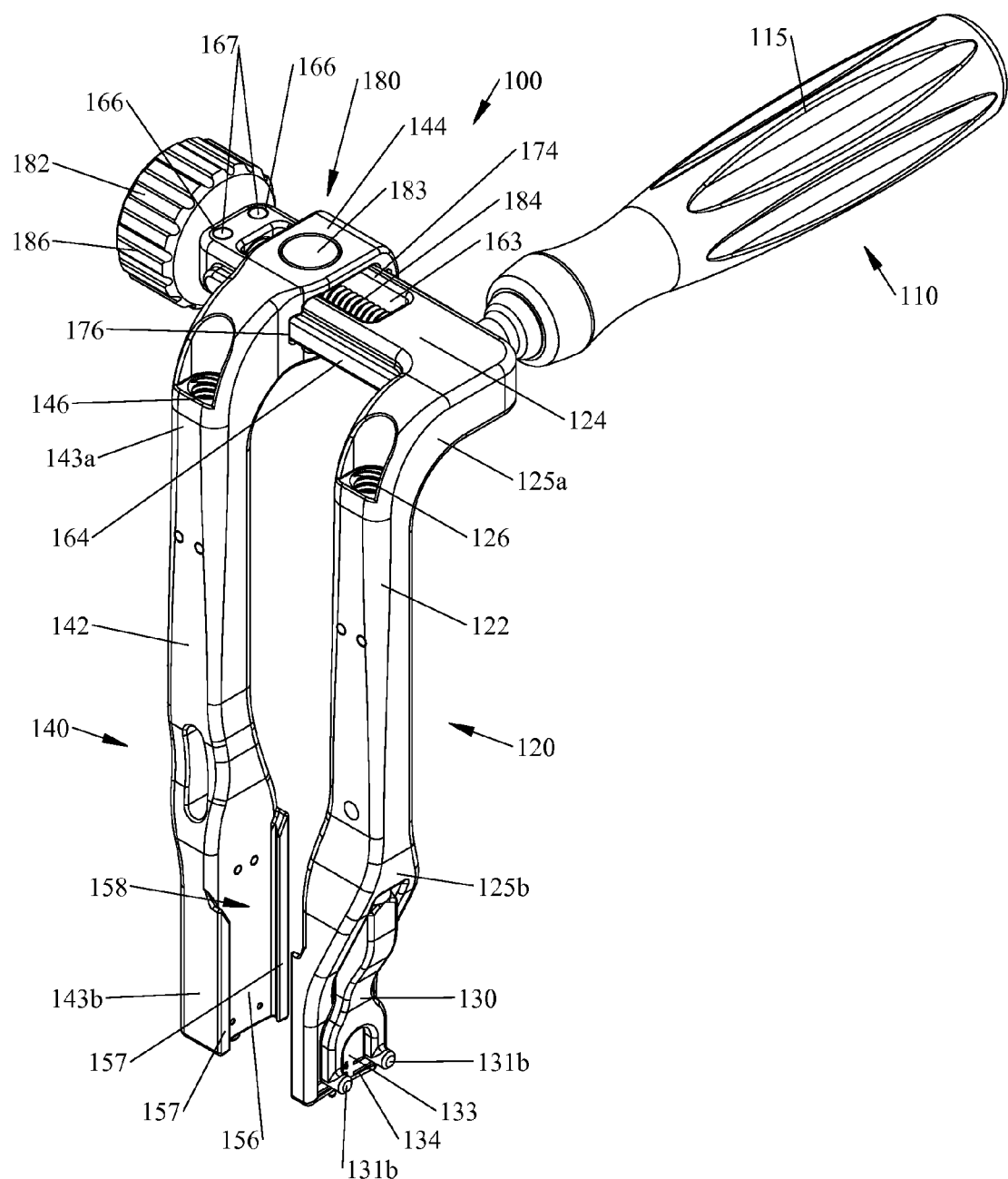
FIG. 1 is a perspective view of an insertion device provided in accordance with the present disclosure.

Embodiments of the presently disclosed devices and methods will now be described in detail with reference to the drawings, wherein like reference numerals identify similar or identical elements. In the drawings and in the description that follows, the term "proximal" will refer to the end of device that is closest to the operator, while the term "distal" will refer to the end of the device that is farthest from the operator. In addition, the term "cephalad" is used in this application to indicate a direction toward a patient's head, whereas the term "caudad" indicates a direction toward the patient's feet. Further still, for the purposes of this application, the term "medial" indicates a direction toward the middle of the body of the patient, whilst the term "lateral" indicates a direction toward a side of the body of the patient (i.e., away from the middle of the body of the patient). The term "posterior" indicates a direction toward the patient's back, and the term "anterior" indicates a direction toward the patient's front. As used herein, a "bone support matrix" is a material that facilitates new bone growth between the opposing vertebral bodies. Suitable bone support matrices can be resorbable or nonresorbable and osteoconductive or osteoinductive. Examples of suitable bone support matrices include synthetic materials, bone morphogenic proteins (BMPs), and heterologous, homologous, or autologous bone and derivatives thereof. The bone support matrix may be radiolucent on x-rays.

Referring to FIGS. 1-5, an insertion device provided in accordance with the present disclosure and configured to facilitate the insertion of an expandable cage, e.g., expandable cage 10 (FIG. 6), into and positioning of the expandable cage 10 (FIG. 6) within the intervertebral space to support adjacent vertebrae is shown generally identified by reference numeral 100. Insertion device 100 includes a handle portion 110, a first engagement arm 120 configured to releasably engage a first support member of an expandable cage, a second engagement arm 140 configured to releasably engage a second support member of an expandable cage, and an adjustment mechanism 180 configured to adjust the relative spacing between first and second engagement arms 120, 140, thereby adjusting the spacing, e.g., expanding or contracting, the first and second support members of the expandable cage relative to one another. Insertion device 100 further includes a clip member insertion tool 200 configured for releasable coupling to insertion device 100 for inserting a clip member between the first and second support members of the expandable cage to retain the expandable cage at a desired height for supporting adjacent vertebrae. Each of these components of insertion device 100 will be described in detail, in turn, below.

Figure 6:
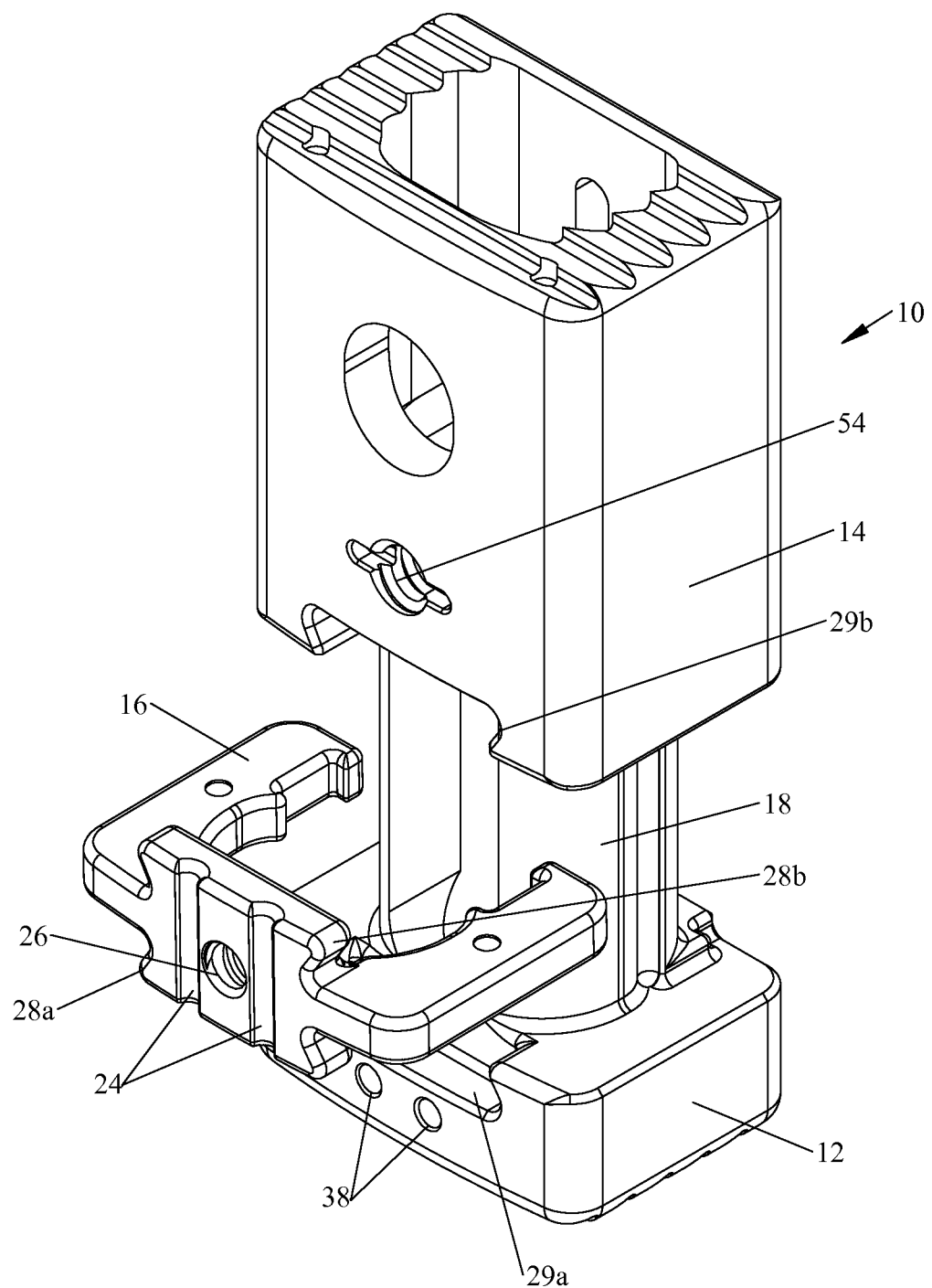
FIG. 6 is a perspective view of an expandable cage configured for use with the insertion device of FIG. 1.

With reference to FIG. 6, an expandable cage 10 configured for use with insertion device 100 (FIG. 1) to facilitate insertion of expandable cage 10 into and positioning of expandable cage 10 within the intervertebral space to support adjacent vertebra is shown. Expandable cage 10 is described in detail in U.S. patent application Ser. No. 12/602,868, filed on Mar. 30, 2009, the entire contents of which are hereby incorporated by reference herein. Thus, description of expandable cage 10 herein will be limited to that which is necessary to facilitate understanding of the use and operation of insertion device 100 (FIG. 1). Further, expandable cage 10 is shown and described herein for exemplary purposes only, as insertion device 100 (FIG. 1) is not limited to use with expandable cage 10. Rather, insertion device 100 (FIG. 1) may be configured for use with any suitable expandable cage.

Expandable cage 10 includes a first support member 12, a second support member 14, and a plurality of variously sized clip members 16 (only one of which is shown) configured for engagement between first and second support members 12, 14. First and second support members 12, 14 are movable relative to one another to vary the height of expandable cage 10. Each of clip members 16 is positionable between first and second support members 12, 14 to maintain first and second support members 12, 14 in various different positions relative to one another that correspond to the various different heights of expandable cage 10.

Figure 7:
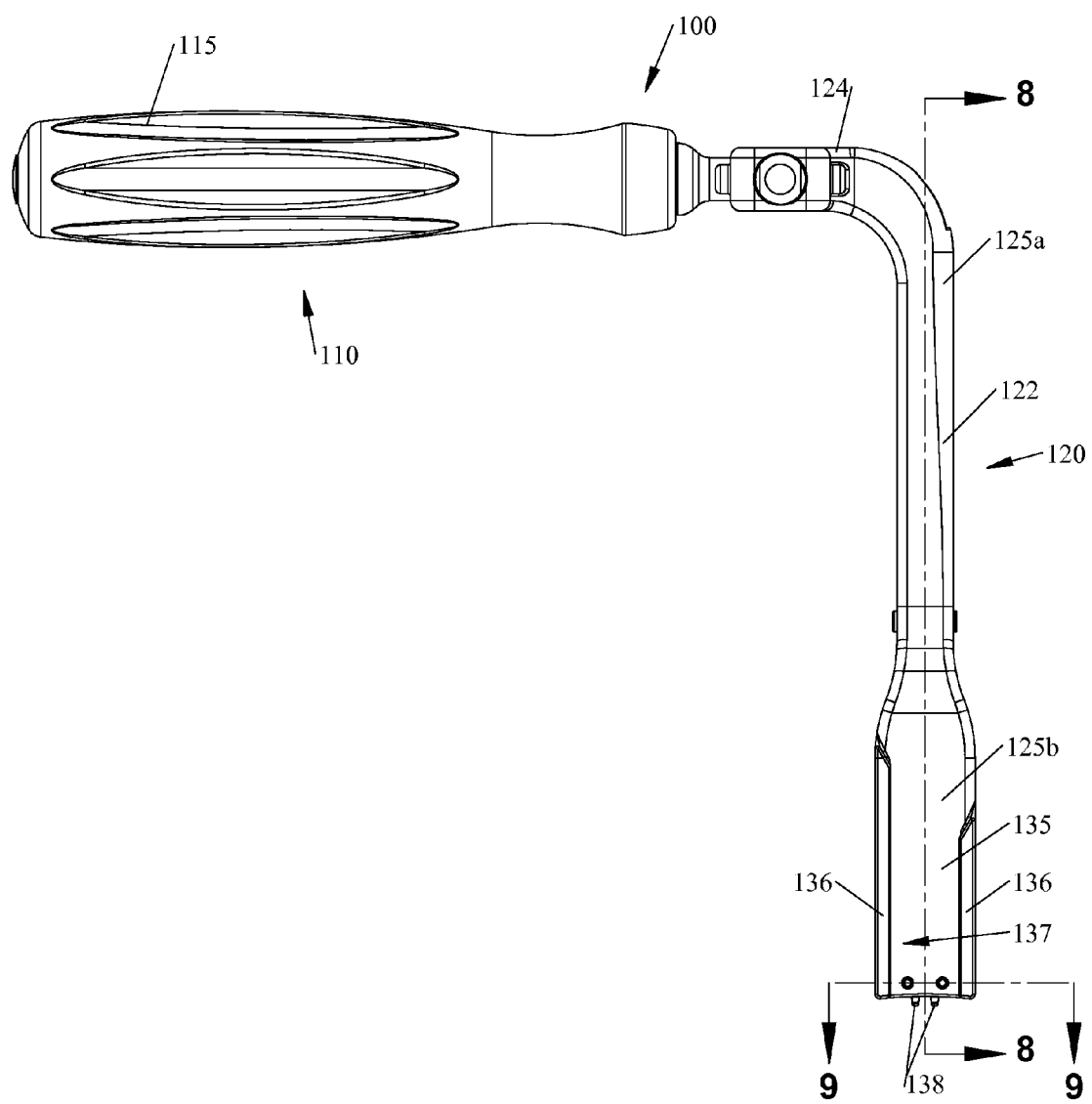
FIG. 7 is an outwardly-directed, side view of the insertion device of FIG. 1 showing the first engagement arm of the insertion device.
Figures 10, 11:
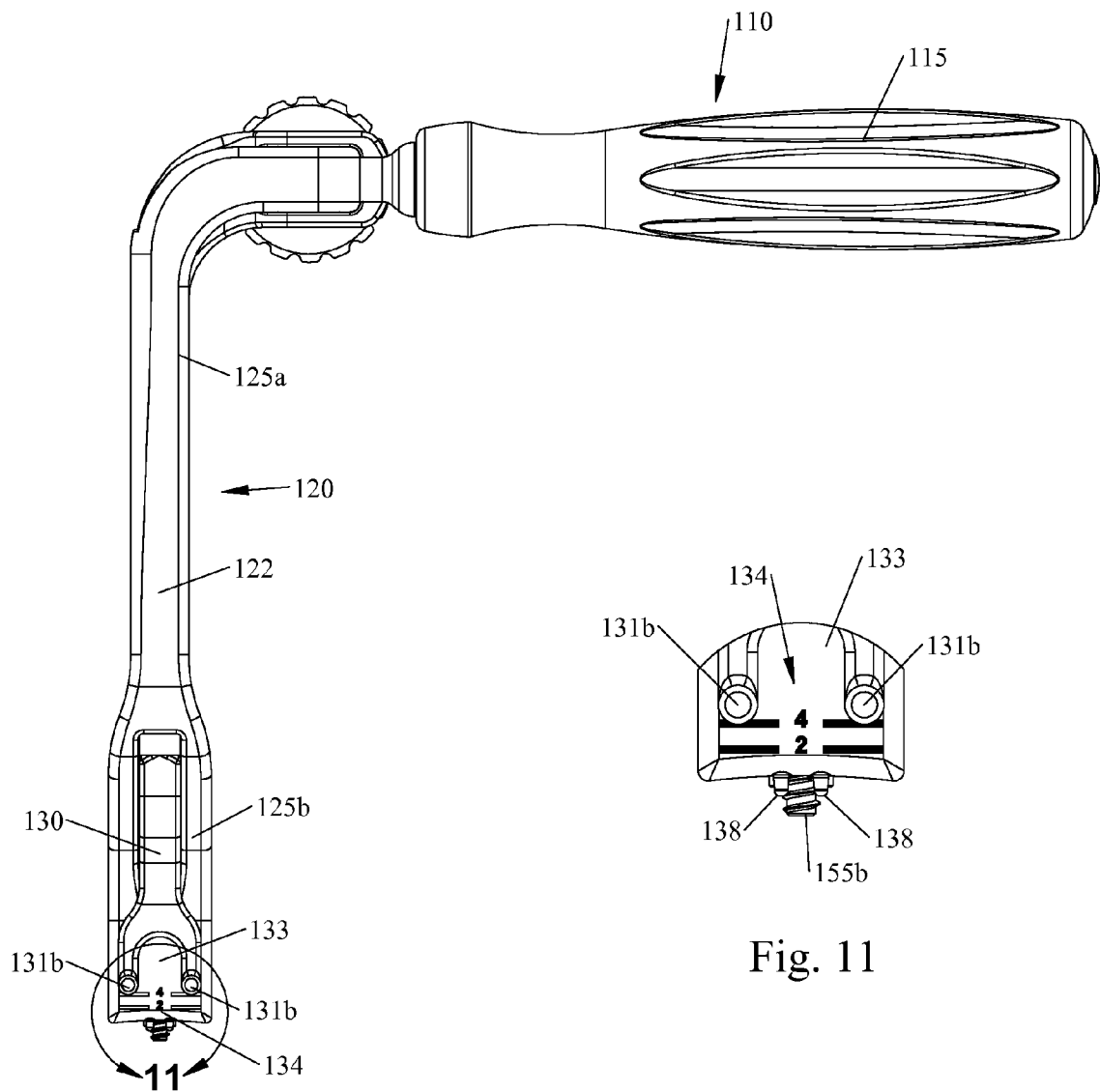
FIG. 10 is an inwardly-directed, side view of the insertion device of FIG. 1 showing the first engagement arm of the insertion device.
FIG. 11 is an enlarged view of the area of detail indicated as "11" in FIG. 10.

Referring to FIGS. 7 and 10, handle portion 110 of insertion device 100 is fixedly engaged to and extends from first engagement arm 120 of insertion device 100. Handle portion 110 defines an ergonomic grip portion 115 configured to facilitate grasping and manipulating insertion device 100.

With reference to FIGS. 7-11, in conjunction with FIGS. 1-6, first engagement arm 120 of insertion device 100 includes a body portion 122 and a lateral extension 124 extending transversely from proximal end 125*a* of body portion 122. Handle portion 110 is engaged to and extends from lateral extension 124 of first engagement arm 120. As will be described in greater detail below, lateral extension 124 is operably coupled to second engagement arm 140 via adjustment mechanism 180 such that the relative spacing between first and second engagement arms 120, 140 may be adjusted as desired.

Body portion 122 of first engagement arm 120 of insertion device 100 defines a proximal end 125*a*, a distal end 125*b*, and a longitudinal bore 126 extending through body portion 122 from the proximal end 125*a* to the distal end 125*b* thereof. Longitudinal bore 126 includes a threaded inner surface 127 disposed towards the proximal end 125*a* of body portion 122 that is configured to engage the threaded distal end 212 of rotation shaft 210 of clip member insertion tool 200, as will be described in greater detail below. A screw member 128 is positioned within longitudinal bore 126 and extends distally from threaded inner surface 127. Screw member 128 includes an engagement recess 129*a* defined at the proximal end thereof. Engagement recess 129*a* is configured to receive a hexalobe driver (not shown) for rotating screw member 128 within body portion 122, although other suitable complementary engagements are also contemplated.

Continuing with reference to FIGS. 7-11, in conjunction with FIGS. 1-6, an indicator stop member 130 is disposed within longitudinal bore 126 towards distal end 125*b* of body portion 122 and extends distally therefrom. The proximal end 131*a* of indicator stop member 130 receives and is threadingly coupled about distal threading 129*b* of screw member 128 such that rotation of screw member 128 in a first direction effects distal translation of indicator stop member 130 and such that rotation of screw member 128 in a second, opposite direction effects proximal translation of indicator stop member 130. A pair of pins 132 is disposed on either side of screw member 128. Each pin 132 is positioned within longitudinal bore 126 and is seated within a groove defined on either side of screw member 128 to maintain screw member 128 in fixed longitudinal position relative to body portion 122.

The distal end of indicator stop member 130, which extends from longitudinal bore 126 of first engagement arm 120 includes a pair of spaced-apart fingers 131*b*. Fingers 131*b* are disposed on an outwardly-facing surface 133 defined at distal end 125*b* of first engagement arm 120 and are configured to abut a proximal surface of a vertebral body during insertion to limit the insertion depth of expandable cage 10 into the intervertebral space. Surface 133 includes markings and/or indicia 134 viewable between the spaced-apart fingers 131*b* of indicator stop member 130 that allow a user to readily ascertain the position of fingers 131*b* of indicator stop member 130 and, thus, the insertion depth limit set via indicator stop member 130. The hexalobe driver (not shown) or other suitable tool configured to engage engagement recess 129*a* of screw member 128 is rotatable to thereby rotate screw member 128 and reposition fingers 13 lb to define a desired insertion depth limit.

Distal end 125*b* of body portion 122 of first engagement arm 120 defines an inwardly-facing surface 135 (opposite surface 133) that includes a pair of rails 136 extending along the outer edges of surface 135. Rails 136 cooperate to define a track 137 that is configured to receive head 222 of clip member engagement portion 220 of clip member insertion tool 20 to facilitate proper alignment of clip member 16 during insertion between first and second support member 12, 14, as will be described in greater detail below. Distal end 125*b* of body portion 122 of first engagement arm 120 further includes a pair of spaced-apart protrusions 138 configured to engage first support member 12 of expandable cage 10 to facilitate the insertion and manipulation of expandable cage 10 into the intervertebral space for supporting adjacent vertebrae.

Referring to FIGS. 12-14, in conjunction with FIGS. 1-6, second engagement arm 140 of insertion device 100 includes a body portion 142 and an extension 144 extending from a proximal end 143*a* of body portion 142. As will be described in greater detail below, extension 144 is operably coupled to lateral extension 124 of first engagement arm 120 via adjustment mechanism 180 such that the relative spacing between first and second engagement arms 120, 140 may be adjusted as desired. Body portion 142 of second engagement arm 140 includes a proximal end 143*a*, a distal end 143*b*, and a longitudinal bore 146 extending through body portion 142 from the proximal end 143*a* to the distal end 143*b* thereof. Body portion 142 defines a non-linear configuration, wherein distal end 143b is offset relative to proximal end 143a via an angled intermediate segment 143c. Longitudinal bore 146 likewise defines a non-linear configuration similar to the configuration of body portion 142.

Longitudinal bore 146 of second engagement arm 140 includes a threaded inner surface 147 disposed towards the proximal end 143a of body portion 142 that is configured to engage the threaded distal end of an engagement tool, e.g., clip member insertion tool 200, similarly as described above with respect to longitudinal bore 126 of first engagement arm 120. A proximal shaft 148 is positioned within longitudinal bore 146 and extends distally from threaded inner surface 147. Proximal shaft 148 includes an engagement recess 149a defined at the proximal end thereof. Engagement recess 149a is configured to receive a hexalobe driver (not shown) for rotating proximal shaft 148 within body portion 142, although other suitable complementary engagements are also contemplated. A pair of pins 152 is disposed on either side of proximal shaft 148. Each pin 152 is positioned within longitudinal bore 146 and is seated within a groove defined on either side of proximal shaft 148 to maintain proximal shaft 148 in fixed longitudinal position relative to body portion 142.

Continuing with reference to FIGS. 12-14, in conjunction with FIGS. 1-6, a linkage 150 is disposed within longitudinal bore 146 adjacent angled intermediate segment 143c of body portion 142. Linkage 150 is pivotably coupled to the distal end of proximal shaft 148 via a pivot pin 149b such that rotation of proximal shaft 148, e.g., via the hexalobe driver (not shown), effects likewise rotation of linkage 150. Linkage 150 is pivotably coupled at its distal end to a distal shaft 154, e.g., via a pivot pin 155a, such that rotation of linkage 150 effects likewise rotation of distal shaft 154. Distal shaft 154 defines a threaded distal end 155b that extend distally from longitudinal bore 146 of body portion 142. As will be described in greater detail below, threaded distal end 155b of distal shaft 154 is configured for engagement with second support member 14 of expandable cage 10 to facilitate the insertion and manipulation of expandable cage 10 into the intervertebral space for supporting adjacent vertebrae.

Distal end 143b of body portion 142 of second engagement arm 140 defines an inwardly-facing surface 156 that includes a pair of rails 157 extending along the outer edges of surface 156. Rails 157 cooperate to define a track 158 that is configured to receive head 222 of clip member engagement portion 220 of clip member insertion tool 200 to facilitate proper alignment of clip member 16 during insertion between first and second support member 12, 14, as will be described in greater detail below. Track 158 may be used in conjunction with, or as an alternative to, track 137 of first engagement arm 120 (see FIGS. 7-11) to facilitate alignment of clip member 16 relative to first and second support members 12, 14 during insertion of clip member 16. That is, clip member 16 and clip member insertion tool 200 may be used with either or both of first and second engagement arms 120, 140 to facilitate positioning of clip member 16 between first and second support members 12, 14.

Figure 2:
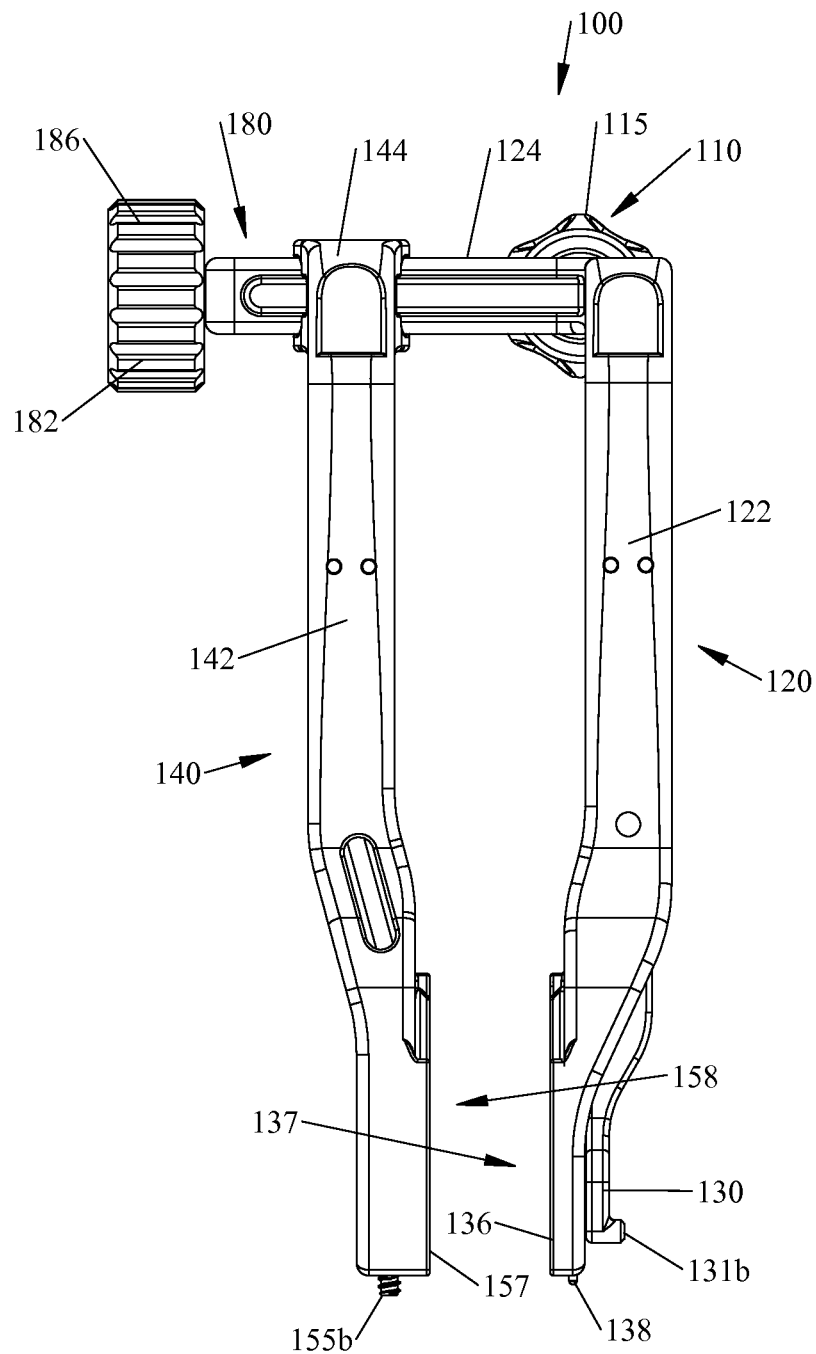
FIG. 2 is a front view of the insertion device of FIG. 1.
Figure 3:
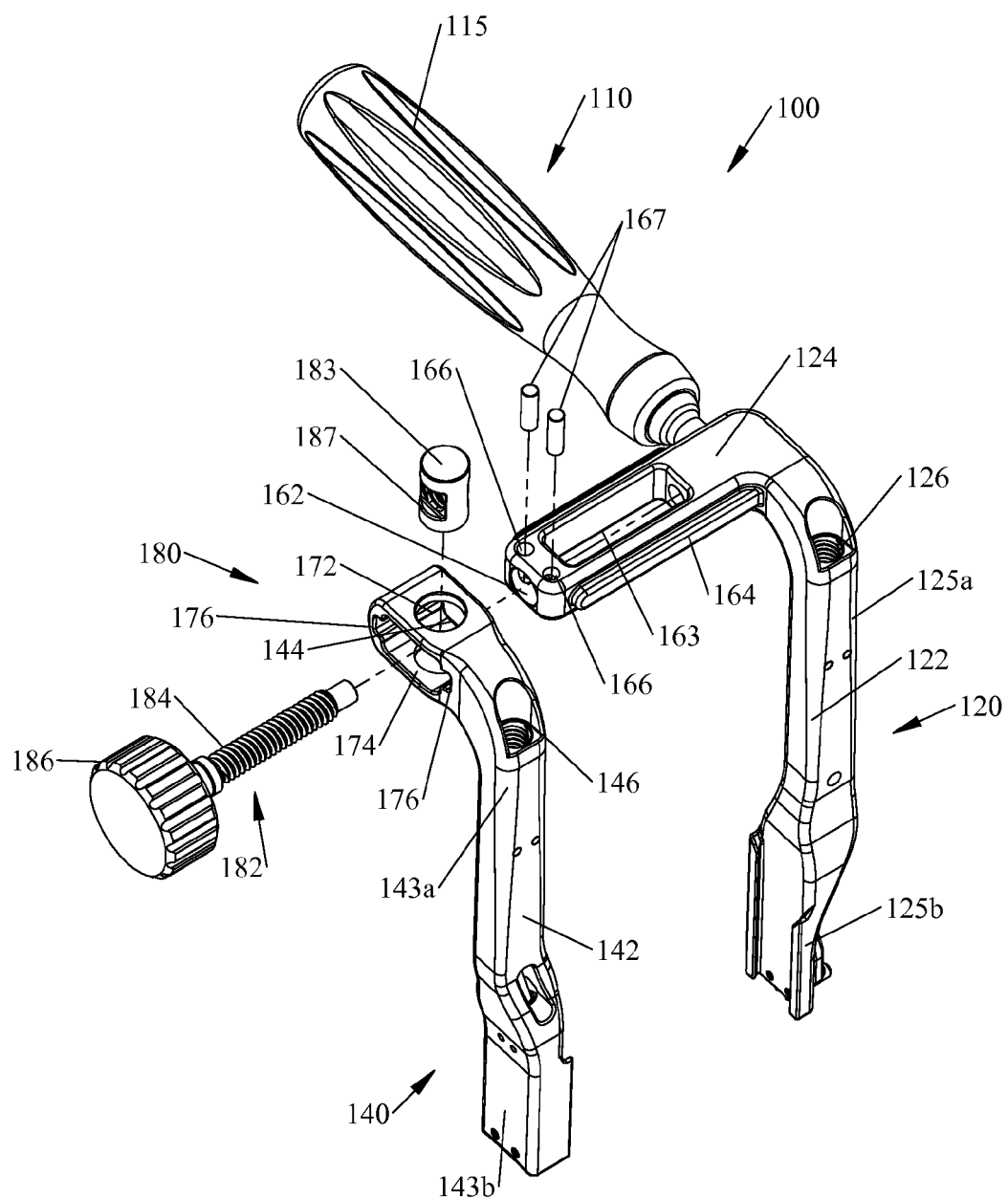
FIG. 3 is an exploded, perspective view of the insertion device of FIG. 1.
Figures 15, 16:
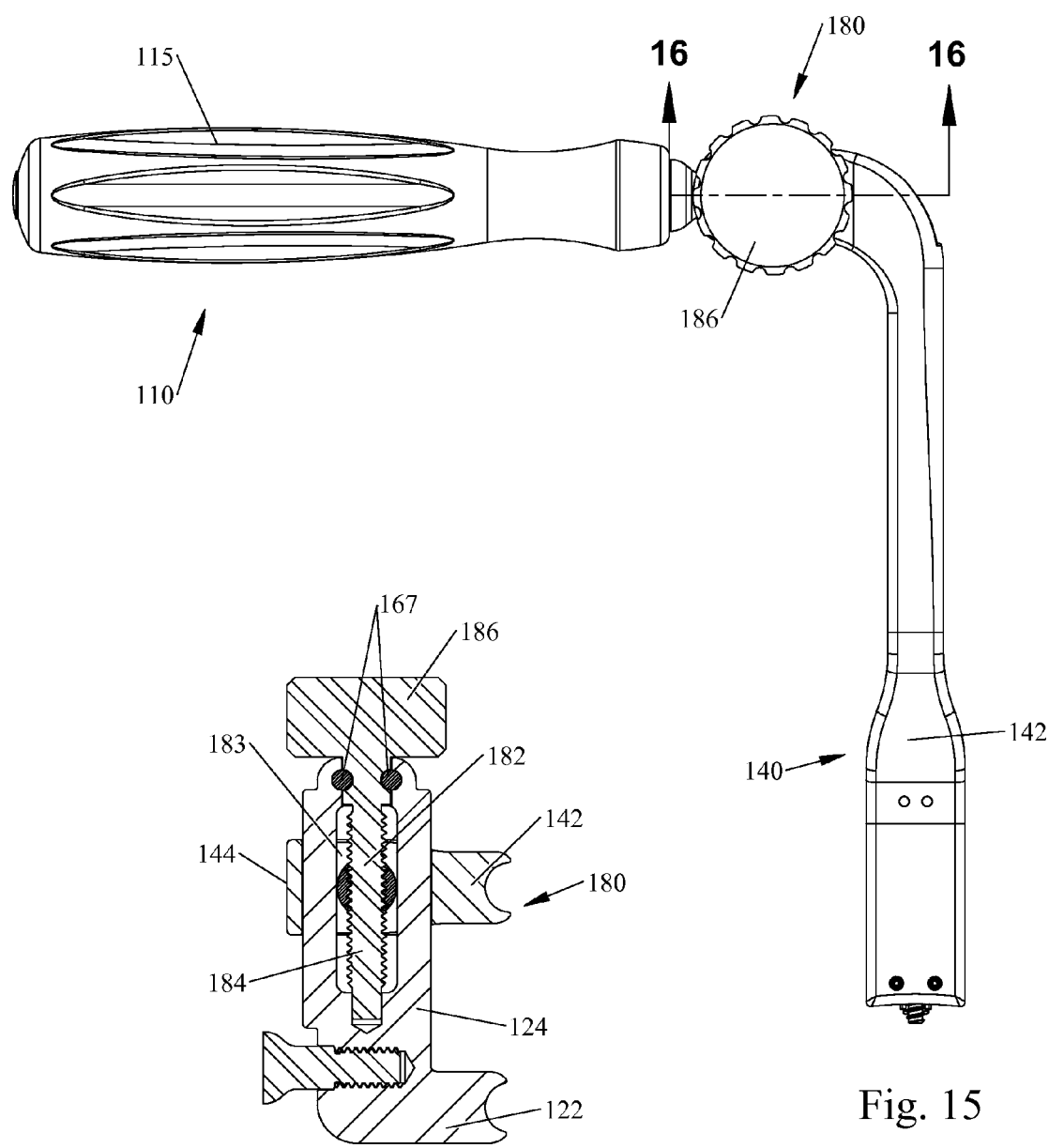
FIG. 15 is an inwardly-directed, side view of the insertion device of FIG. 1 showing the second engagement arm of the insertion device.
FIG. 16 is a cross-sectional view taken along section line 16-16 of FIG. 15.

With reference to FIGS. 15-16, in conjunction with FIGS. 1-3, adjustment mechanism 180 operably couples lateral extension 124 of first engagement arm 120 and extension 144 of second engagement arm 140 to one another to permit selective adjustment of the relative spacing between first and second engagement arms 120, 140, thereby adjusting the spacing, e.g., expanding or contracting, the first and second support members of the expandable cage relative to one another. Adjustment mechanism 180 includes an adjustment screw 182 and an adjustment cylinder 183. Adjustment screw 182 has a threaded shank 184 and a head 186 ergonomically configured to facilitate grasping and rotating adjustment screw 182. Adjustment cylinder 183 includes a threaded transverse passageway 187 that is configured to threadingly receive threaded shank 184 of adjustment screw 182 such that rotation of adjustment screw 182 in a first direction relative to adjustment cylinder 183 urges adjustment cylinder 183 to translate along adjustment screw 182 away from head 186 and such that rotation of adjustment screw 182 in a second, opposite direction relative to adjustment cylinder 183 urges adjustment cylinder 183 to translate along adjustment screw 182 towards head 186.

Lateral extension 124 of first engagement arm 120 defines a central bore 162, pair of opposed slots 163 extending through lateral extension 124 and communication with central bore 162, a pair of ribs 164 extending along the sides of lateral extension 124, and a pair of apertures 166 disposed towards the free end of lateral extension 124. Central bore 162 is configured to receive threaded shank 184 of adjustment screw 182. Adjustment cylinder 183 is configured to extend through slots 163 and central bore 162, which extends between slots 163. Apertures 166 are configured to receive pins 167 to secure adjustment screw 182 in fixed position relative to lateral extension 124 while still permitting rotation of adjustment screw 182 relative to lateral extension 124.

Extension 144 of second engagement arm 140 defines a cylindrical passageway 172 that is configured to secure adjustment cylinder 183 therein and a transverse opening 174 that is configured to slidably receive lateral extension 124 of first engagement arm 120. Extension 144 further defines a pair of opposing grooves 176 on the internal surface thereof that is defined by transverse opening 174. Grooves 176 are configured to receive ribs 164 of lateral extension 124 to guide translation of extension 144 along lateral extension 124 between the free and fixed ends of lateral extension 124. Thus, with extension 144 disposed about lateral extension 124, adjustment cylinder 163 secured within transverse opening 174 of extension 144, and adjustment screw 182 translatably fixed relative to lateral extension 124, rotation of adjustment screw 182 may be effected to urge extension 144 along lateral extension 124 between the free and fixed ends of lateral extension 124, thereby varying the spacing between first and second engagement arms 120, 140.

Figure 4:
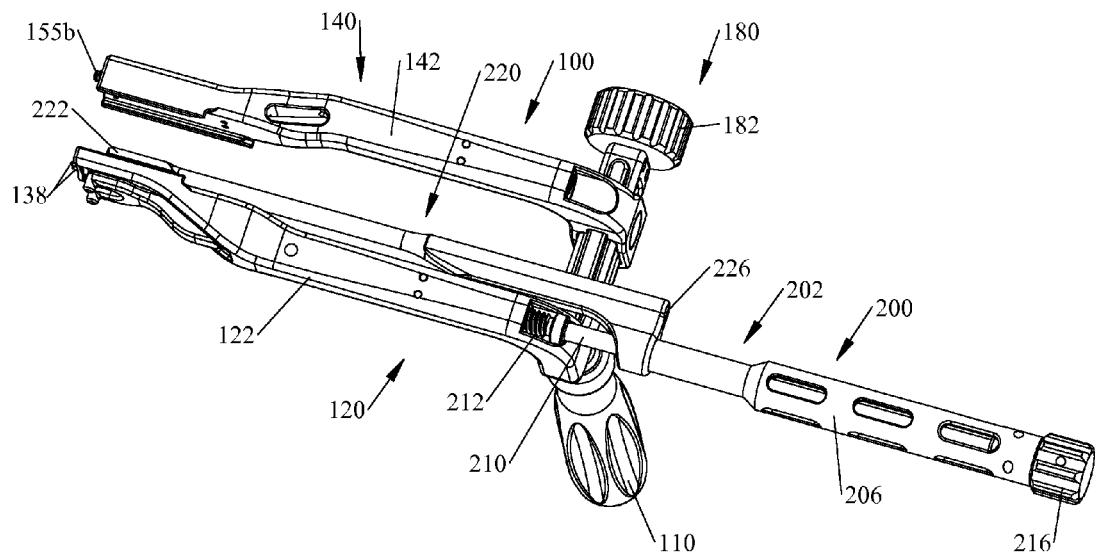
FIG. 4 is a perspective view of the insertion device of FIG. 1 including a clip member insertion tool coupled thereto.
Figure 5:
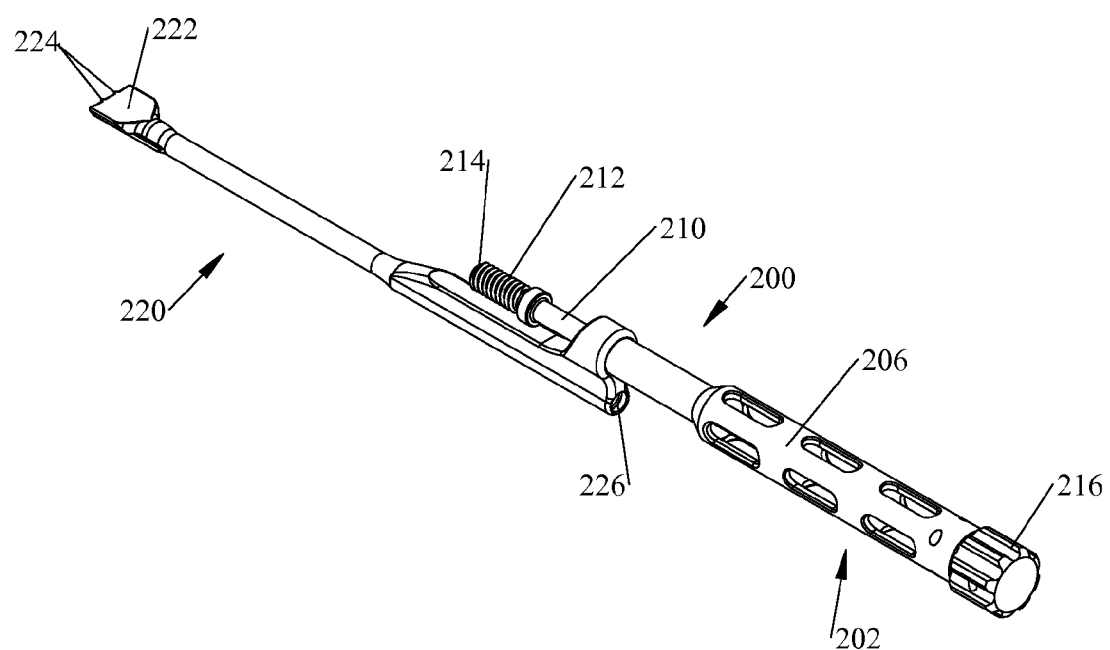
FIG. 5 is a perspective view of the clip member insertion tool of FIG. 4.

Referring to FIGS. 4-5, in conjunction with FIG. 6, clip member insertion tool 200, as mentioned above, is releasably engagable with insertion device 100 to facilitate the insertion of clip member 16 between first and second support members 12, 14 of expandable cage 10. Clip member insertion tool 200 includes an insertion device engagement portion 202 and a clip member engagement portion 220. Insertion device engagement portion 202 includes an outer housing 206 and a rotation shaft 210 rotatably disposed within outer housing 206. Rotation shaft 210 includes a threaded distal end 212 defining a distal tip 214. Rotation shaft 210 further includes a rotation knob 216 disposed at the proximal end thereof and extending proximally from outer housing 206. Rotation knob 216 is selectively rotatable to facilitate engagement of rotation shaft 210 within longitudinal bore 126 (FIG. 8) of first engagement arm 120 of insertion device 100.

Clip member engagement portion 220 of clip member insertion tool 200 is engaged to outer housing 206 of insertion device engagement portion 202 and extends distally therefrom. Clip member engagement portion 220 defines a head 222 at the distal end thereof that includes a pair of protrusions 224 configured to couple to clip member 16 to facilitate insertion of clip member 16 between first and second support member 12, 14 of expandable cage 10, as will be described in greater detail below. Head 222 is configured for complementary sliding engagement within tracks 137, 158, as noted above. Clip member engagement portion 220 may also be configured to releasably engage outer housing 206 of insertion device engagement portion 202 such that insertion device engagement portion 202 may also be used to engage second engagement arm 140 of insertion device 100 with second support member 14 of expandable cage 10, although removal of clip member engagement portion 220 from clip member insertion tool 200 is not necessary for this purpose.

Figure 17:
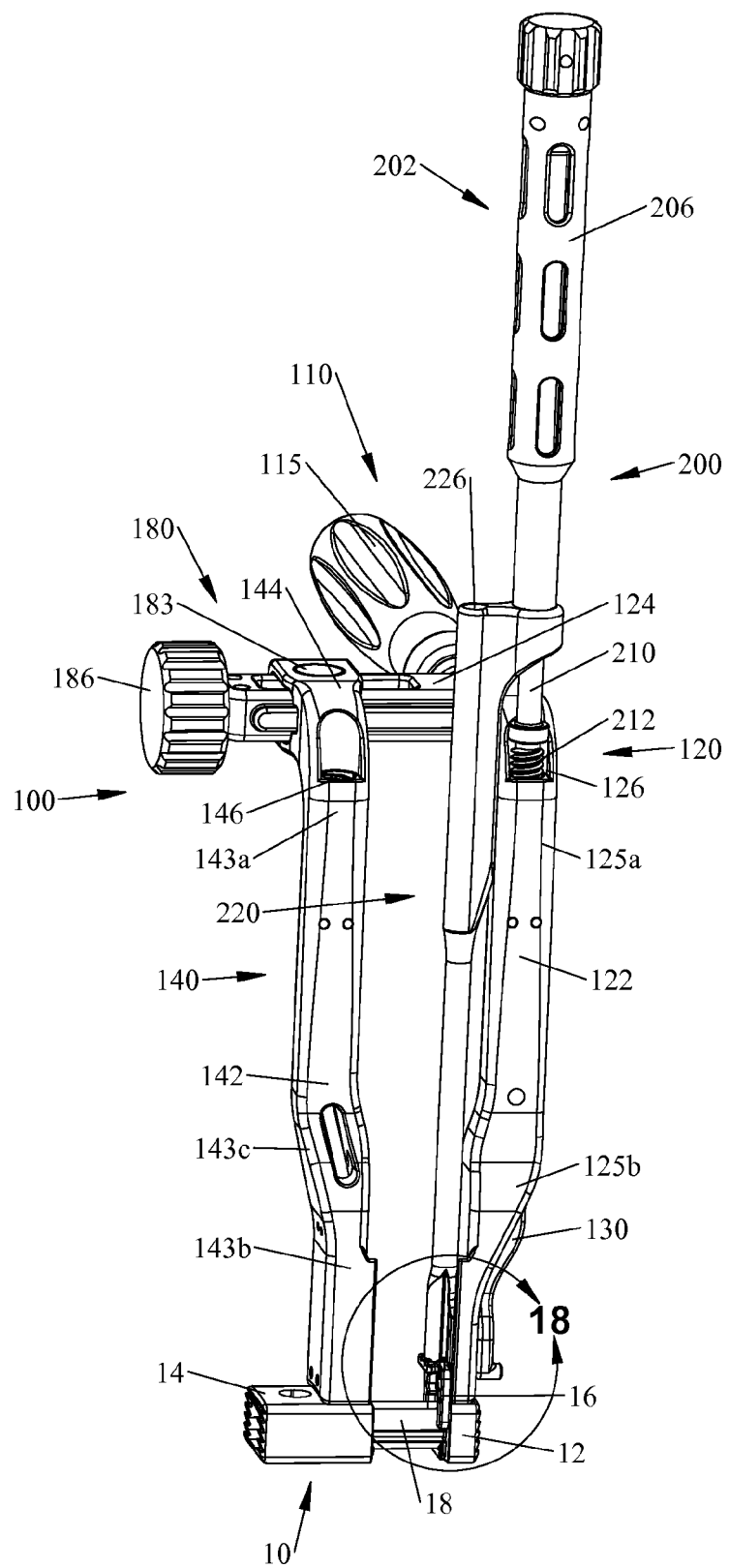
FIG. 17 is a side view of the insertion device of FIG. 1, including the clip member insertion tool of FIG. 5, coupled to the expandable cage of FIG. 6.
Figure 18:
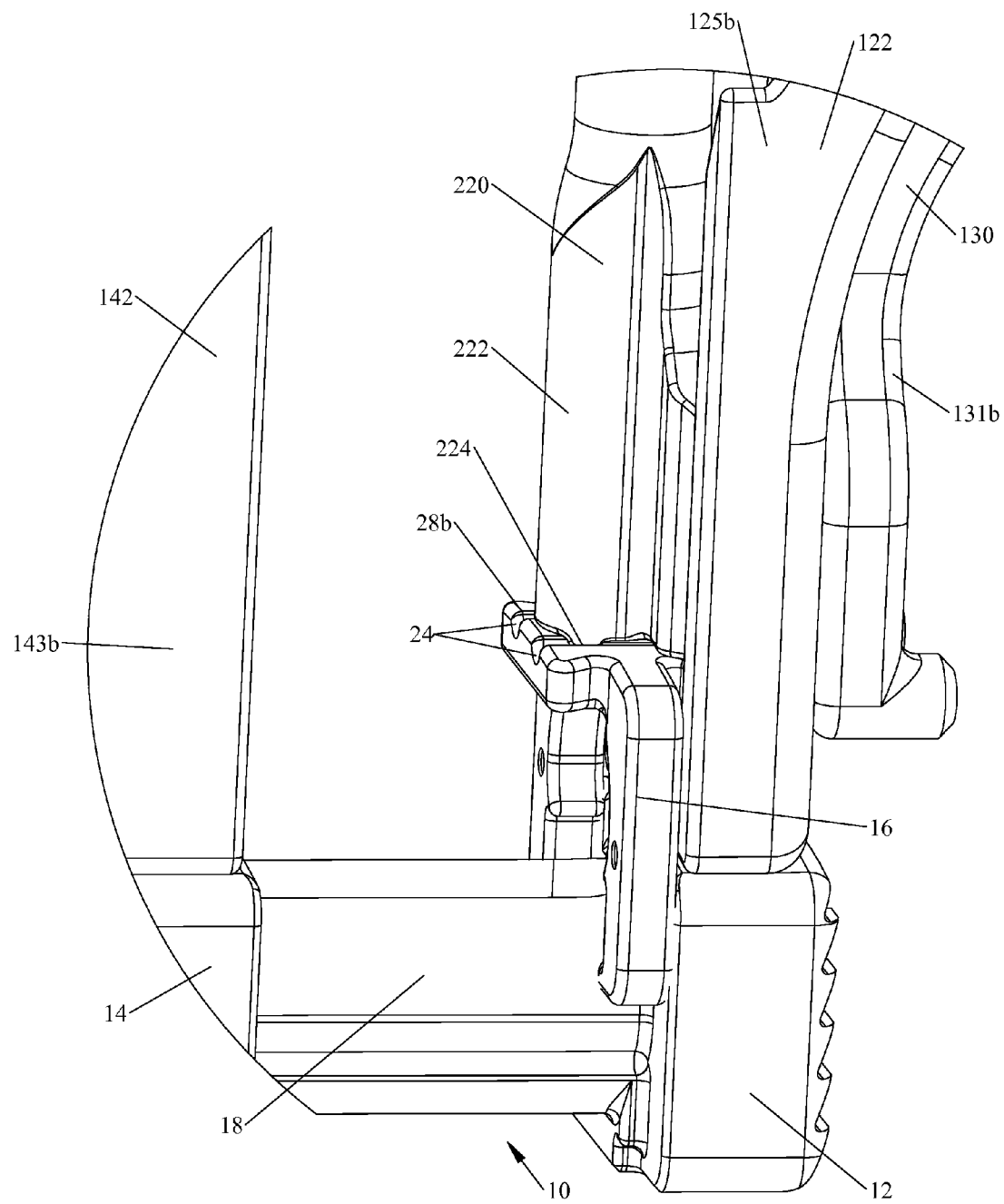
FIG. 18 is an enlarged view of the area of detail indicated as "18" in FIG. 17.

Turning now to FIGS. 17-18, in conjunction with FIGS. 1-16, the use of insertion device 100 to insert and position expandable cage 10 within the intervertebral space for support adjacent vertebrae is described. Initially, the hexalobe driver (not shown) is engaged within engagement recess 129*a* of screw member 128 to rotate screw member 128 and thereby reposition fingers 131*b* to set indicator stop member 130 to the desired insertion depth limit. Thereafter, first and second engagement arms 120, 140 of insertion device 100 are engaged to first and second support members 12, 14, respectively, of expandable cage 10. More specifically, first engagement arm 120 is approximated relative to first support member 12 such that spaced-apart protrusions 138 formed at distal end 125*b* of body portion 122 of first engagement arm 120 are received within corresponding spaced-apart apertures 38 defined within first support member 12. Second engagement arm 140 is approximated relative to second support member 14 such that threaded distal end 155*b* of distal shaft 154 is positioned adjacent threaded aperture 54 of second support member 14. The hexalobe driver (not shown) is then inserted through longitudinal bore 146 of second engagement 140 sufficiently so as to engage proximal shaft 148 of second engagement arm 140. With the hexalobe driver (not shown) engaged with proximal shaft 148, the hexalobe driver (not shown) may be rotated to thereby rotate proximal shaft 148, linkage 150, and distal shaft 154. Rotation of distal shaft 154 relative to threaded aperture 54 of second support member 14 threadingly engages threaded distal end 155*b* of distal shaft 154 of second engagement arm 140 within threaded aperture 54 of second support member 14, thereby engaging second support member 14 to second engagement arm 140.

With insertion device 100 coupled to expandable cage 10 as described above, and after removing the diseased or damaged vertebral tissue from the intervertebral space, expandable cage 10 is advanced into the intervertebral space, e.g., using handle portion 110 of insertion device 100, into position between adjacent vertebrae. Once expandable cage 10 has been positioned in the desired location, the relative spacing between first and second engagement arms 120, 140 is adjusted, e.g., via rotating head 186 of adjustment screw 182, to thereby adjust the relative height of expandable cage 10 for proper fitting between the adjacent vertebrae. As can be appreciated, upon insertion of expandable cage 10 to the appropriate depth, fingers 131*b* of indicator stop member 130 contact one of the adjacent vertebrae to inhibit expandable cage 10 from being inserted further, thus ensuring that expandable cage 10 is inserted into the intervertebral space to the appropriate depth.

With expandable cage 10 positioned within the intervertebral space and expanded to the appropriate height, clip member 16 is ready for installation between first and second support members 12, 14 to fix the height of expandable cage 10. Depending on the height required, an appropriately sized clip member 16 is selected from a plurality of clip members 16 of varying height. The appropriately sized clip member 16 is then coupled to clip member insertion tool 200. More specifically, protrusions 224 of head 222 of clip member engagement portion 220 of clip member insertion tool 200 are inserted into vertical slots 24 defined within clip member 16. Head 222 of clip member engagement portion 220 may additionally or alternatively include a threaded extension (not shown) configured for engagement within threaded aperture 26 of clip member 16, or an additional tool (not shown) may be inserted through longitudinal bore 226 of clip member engagement portion 220 for similar purposes.

Next, head 222 of clip member insertion tool 200 is slid distally along first engagement arm 120 of insertion device 100 adjacent inner surface 135 such that first head 222 of clip member engagement portion 220 of clip member insertion tool 200 is slidably received between rails 136 and is guided along track 137 defined at the distal end of first engagement arm 120. More specifically, threaded distal end 212 of rotation shaft 210 of clip member insertion tool 200 is engaged within longitudinal bore 126 of first engagement arm 120 and is advanced into longitudinal bore 126 via rotation of rotation knob 216 to thereby translate clip member engagement portion 220 and, thus, clip member 216, distally along track 137 of first engagement arm 120. The engagement of head 222 with track 137 maintains proper alignment of clip member 216.

Clip member 16 is advanced distally eventually such that first engagement projection 28a is guided into engagement within engagement recess 29*a* of first support member 12 and is clipped, or engaged about column 18 of expandable cage 10. Additionally or alternatively, head 222 of clip member engagement portion 220 of clip member insertion tool 200 is slidably engaged within track 158 of second engagement arm 140 to guide second engagement projection 28b into engagement within engagement recess 29*b* of second support member 14. Once clip member 16 is secured between first and second support members 12, 14 to retain the height of expandable cage 10 for supporting adjacent vertebrae, insertion device 100, including clip member insertion tool 200, may be disengaged from expandable cage 10 (in opposite fashion as described above with respect to the engagement of insertion device 100 and clip member insertion tool 200 to expandable cage 10) and removed from the surgical site.

Figure 19:
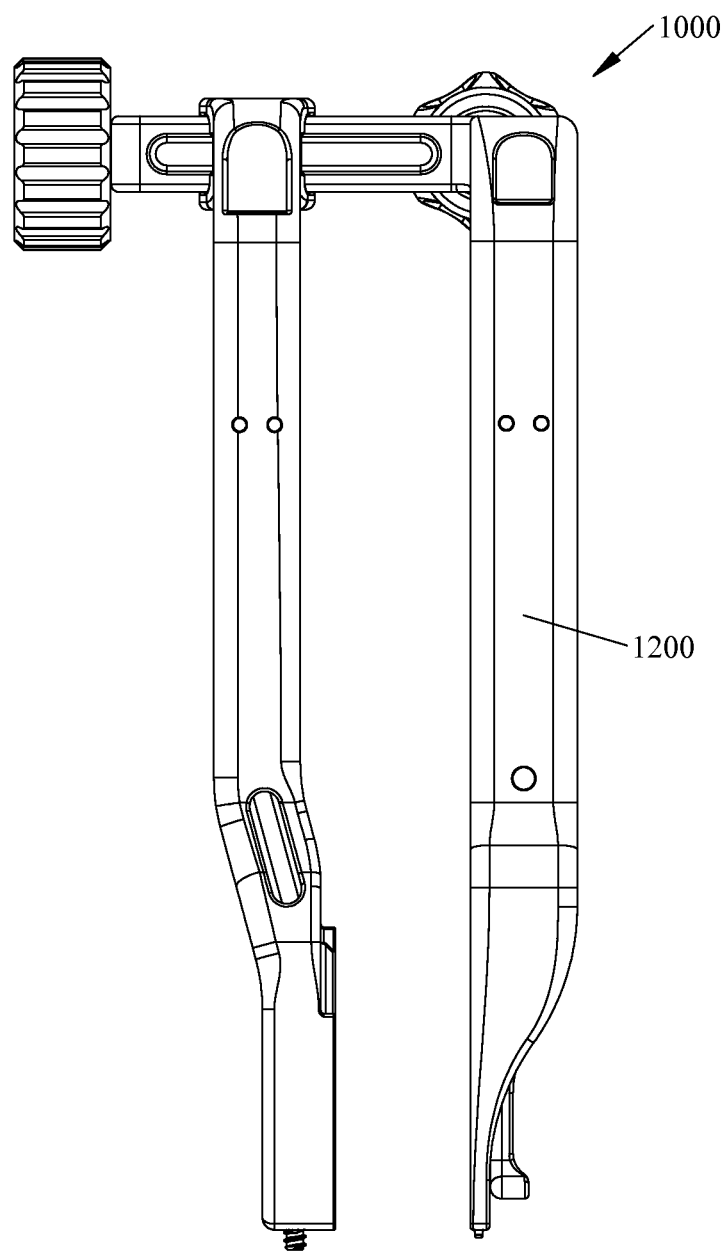
FIG. 19 is a front view of another insertion device provided in accordance with the present disclosure.
Figure 20:
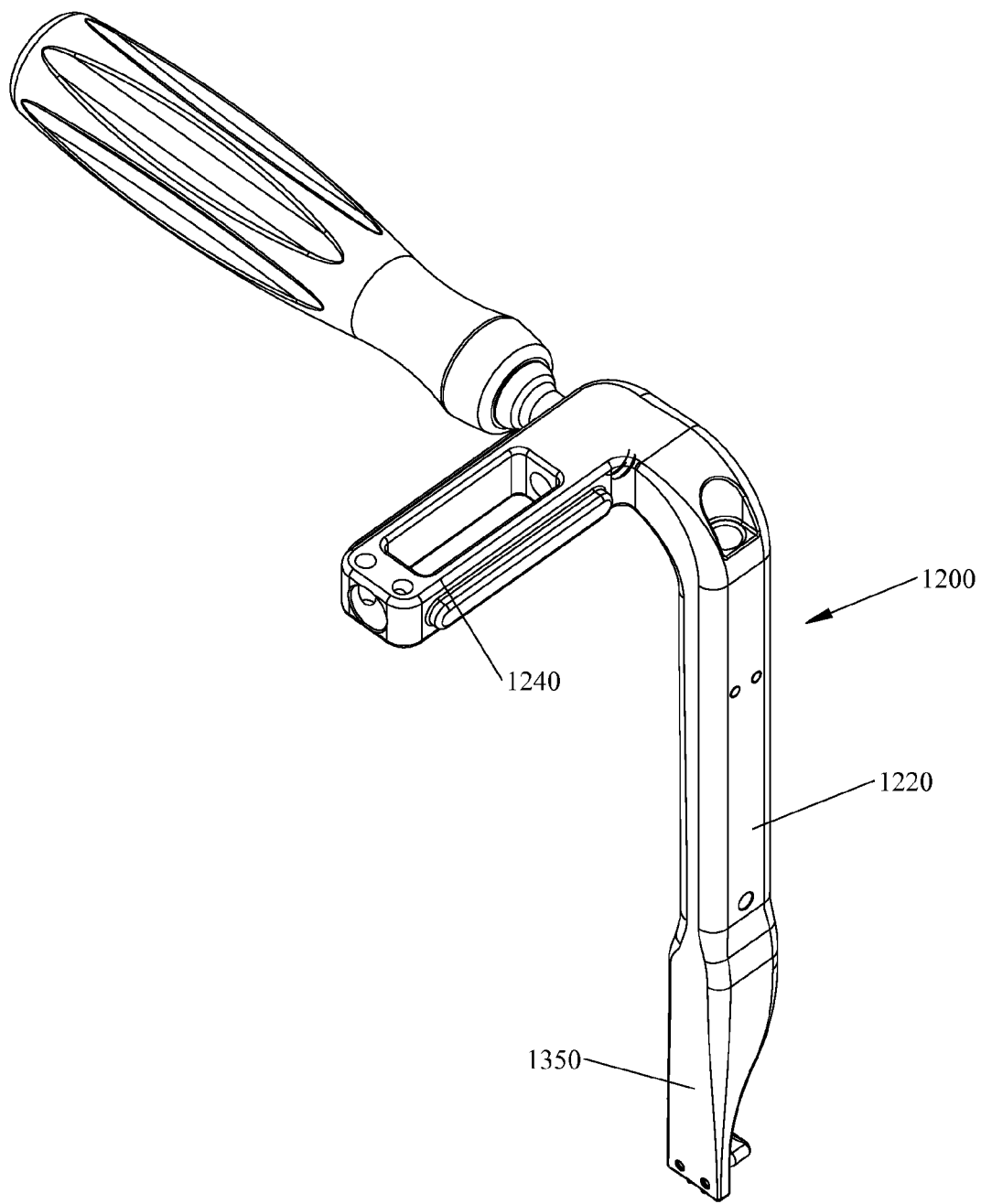
FIG. 20 is a perspective view of the first engagement arm of the insertion device of FIG. 19.

Turning now to FIGS. 19 and 20, another embodiment of an insertion device provided in accordance with the present disclosure and configured to facilitate the insertion of an expandable cage, e.g., expandable cage 10 (FIG. 6), into and positioning of the expandable cage 10 (FIG. 6) within the intervertebral space to support adjacent vertebrae is shown generally identified by reference numeral 1000. Insertion device 1000 is similar to and may include any of the features of insertion device 100 (FIGS. 1-5). Accordingly, only the differences between insertion device 1000 and insertion device 100 (FIGS. 1-5) will be described in detail below for purposes of brevity.

First engagement arm 1200 of insertion device 1000, as best shown in FIG. 20, includes a body portion 1220 and a lateral extension 1240 extending transversely from the proximal end of body portion 1220. Body portion 1220 defines an inwardly-facing surface 1350. However, rather than providing rails 136 as detailed above with respect to body portion 122 of insertion device 100 (see FIG. 7), body portion 1220 of first engagement arm 1200 of insertion device 1000 defines a flat inwardly-facing surface 1350. Providing a flat inwardly-facing surface 1350 without rails allows for the distal portion of body portion 1220 to define a reduced thickness (see FIG. 19) which facilitates visualization into the intervertebral space. The use and operation of insertion device 1000 is similar to that of insertion device 100 (FIG. 1) detailed above.

It will be understood that various modifications may be made to the embodiments of the presently disclosed insertion device. Therefore, the above description should not be construed as limiting, but merely as exemplifications of embodiments. Those skilled in the art will envision other modifications within the scope and spirit of the present disclosure.

What is claimed is:

1. An insertion device configured for use in spinal surgery, the insertion device comprising:
    a first engagement arm including a first body portion and a first proximal extension, the first body portion configured to engage a first support member of an expandable cage;
    a second engagement arm including a second body portion and a second proximal extension, the second body portion configured to engage a second support member of the expandable cage, the second proximal extension disposed about the first proximal extension and slidable therealong from a free end of the first proximal extension to a fixed end of the first proximal extension to vary a spacing between the first and second engagement arms; and
    an adjustment mechanism operably coupling the first and second proximal extensions of the respective first and second engagement arms to one another, the adjustment mechanism including:
        an adjustment screw rotatably coupled to the first proximal extension, the adjustment screw including a shank defining threading; and
        an adjustment cylinder coupled to the second proximal extension, the adjustment cylinder defining a threaded passageway configured to receive the shank of the adjustment screw in threaded engagement therewith, wherein rotation of the adjustment crew relative to the adjustment cylinder urges the second proximal extension to translate along the first proximal extension to vary the spacing between the first and second engagement arms.

2. The insertion device according to claim 1, wherein the adjustment screw further includes a head configured to facilitate rotation of the adjustment screw relative to the adjustment cylinder.

3. The insertion device according to claim 1, wherein the first engagement arm includes at least one protrusion configured for engagement within at least one aperture defined within the first support member of the expandable cage to engage the first support member at a distal end of the first engagement arm.

4. The insertion device according to claim 1, wherein the second engagement arm includes a distal shaft extending distally from the second engagement arm, the distal shaft including a threaded distal end configured for engagement within a threaded aperture defined within the second support member of the expandable cage to engage the second support member at a distal end of the second engagement arm.

5. The insertion device according to claim 4, wherein the second engagement arm defines a longitudinal bore extending therethrough, and wherein the distal shaft is disposed partially within and extends distally from the longitudinal bore, the longitudinal bore further including a proximal shaft disposed therein and a linkage member disposed therein, the linkage member interconnecting the proximal and distal shafts.

6. The insertion device according to claim 5, wherein the proximal and distal shafts are laterally offset relative to one another and wherein the linkage member transfers rotational motion of the proximal shaft to rotational motion of the distal shaft.

7. The insertion device according to claim 5, wherein the linkage member transfers rotational motion of the proximal shaft to rotational motion of the distal shaft and wherein the longitudinal bore of the second engagement arm is configured to receive an engagement tool configured to rotate the proximal shaft, thereby rotating the linkage member and the distal shaft for threadingly engaging the threaded distal end of the distal shaft with the threaded aperture of the second support member.

8. The insertion device according to claim 1, wherein the first engagement arm defines a longitudinal bore extending therethrough, the longitudinal bore including a screw member disposed therein and an indicator stop member partially disposed therein and extending distally therefrom, the screw member and the indicator stop member coupled to one another such that rotation of the screw member effects translation of the indicator stop member relative to the first engagement arm to set an insertion depth limit of the expandable cage within an intervertebral space.

9. The insertion device according to claim 8, wherein the longitudinal bore of the first engagement arm is configured to receive a driver configured to rotate the screw member, thereby translating the indicator stop member relative to the first engagement arm.

10. The insertion device according to claim 8, wherein the indicator stop member visually indicates the insertion depth limit of the expandable cage within the intervertebral space.

11. The insertion device according to claim 1, further comprising an engagement tool including a clip member engagement portion configured to couple to a clip member of the expandable cage at a distal end of the clip member engagement portion.

12. The insertion device according to claim 11, wherein at least one of the first and second engagement arms defines a track configured to guide insertion of the engagement tool to guide the clip member between the first and second support members of the expandable cage.

13. The insertion device according to claim 1, further comprising a handle portion extending from one of the first and second engagement arms, the handle portion configured to facilitate manipulation of the insertion device.

14. A method of performing spinal surgery, comprising:
    preparing an intervertebral space;
    engaging first and second engagement arms of an insertion device to first and second support members, respectively, of an expandable cage;
    advancing the expandable cage, under control of the insertion device, into the intervertebral space;
    adjusting a relative spacing between the first and second engagement arms to adjust a height of the expandable cage within the intervertebral space;
    coupling a clip member to a clip member insertion tool;
    moving the clip member insertion tool relative to the insertion device such that at least a portion of the clip member insertion tool is guided by the insertion device to guide the clip member into engagement between the first and second support members of the expandable cage;

disengaging the clip member insertion tool from the clip member and withdrawing the clip member insertion tool; and disengaging the first and second engagement arms of the insertion device from the first and second support members of the expandable cage and withdrawing the insertion device.

* * * * *